US012673195B2

(12) United States Patent
Stevens et al.

(10) Patent No.: US 12,673,195 B2
(45) Date of Patent: Jul. 7, 2026

(54) SEPARATE POSITIONABLE HEMOSTASIS VALVE FOR IMPLANTABLE MEDICAL LEAD INTRODUCER HUB

(71) Applicant: Medtronic, Inc., Minneapolis, MN (US)

(72) Inventors: Derek M. Stevens, Chanhassen, MN (US); Kevin Seifert, Forest Lake, MN (US)

(73) Assignee: Medtronic, Inc., Minneapolis, MN (US)

( * ) Notice: Subject to any disclaimer, the term of this patent is extended or adjusted under 35 U.S.C. 154(b) by 852 days.

(21) Appl. No.: 18/050,886

(22) Filed: Oct. 28, 2022

(65) Prior Publication Data

US 2024/0139488 A1     May 2, 2024

(51) Int. Cl.
*A61M 39/06* (2006.01)
*A61M 39/02* (2006.01)
(Continued)

(52) U.S. Cl.
CPC ............... *A61M 39/06* (2013.01); *A61N 1/05* (2013.01); *A61N 1/37516* (2017.08); *A61N 1/37518* (2017.08); *A61M 2039/0258* (2013.01); *A61M 2039/0626* (2013.01); *A61M 2039/0673* (2013.01)

(58) Field of Classification Search
CPC .......... A61M 39/06; A61M 2039/0258; A61M 2039/0626; A61M 2039/0673; A61N 1/37516; A61N 1/37518; A61N 1/05
See application file for complete search history.

(56) References Cited

U.S. PATENT DOCUMENTS 5,098,391 A     3/1992   Pantages et al.
6,723,073 B2   4/2004   Ley et al.
(Continued)

FOREIGN PATENT DOCUMENTS

WO          2009073754 A2     6/2009
WO      WO-2022173997 A1 *  8/2022   ........... A61F 2/2436

OTHER PUBLICATIONS

Pressure Products Medical Supplies, Inc., "Pressure Products", 2 pp., Retrieved from the Internet on Jan. 26, 2023 from URL: https://www.pressure-products.com/wip/.
(Continued)

*Primary Examiner* — Carl H Layno
*Assistant Examiner* — Aya Ziad Bakkar
(74) *Attorney, Agent, or Firm* — Shumaker & Sieffert, P.A.

(57) ABSTRACT

A medical system including an implantable medical, the lead comprising a lead body and a helical electrode at least one of extending or extendable from a distal end of the lead body. The medical system including a hemostasis valve coupled to the lead body proximal the distal end of the lead body, the hemostasis valve configured to slide along the lead body. The distal end of the lead body is configured for insertion into an introducer hub positioned in an opening into a vasculature of a patient and the lead body configured for subsequent advancement through the introducer hub to facilitate securing the hemostasis value to the introducer hub. The hemostasis valve is configured for slidable advancement of the lead body therethrough for continued advancement of the lead body through the introducer hub.

29 Claims, 8 Drawing Sheets

(51) Int. Cl.
　　　*A61N 1/05*　　　　　(2006.01)
　　　*A61N 1/375*　　　　(2006.01)

(56) References Cited

U.S. PATENT DOCUMENTS

| | | | |
|---|---|---|---|
| 6,758,854 B1 | 7/2004 | Butler | |
| 8,142,446 B2 | 3/2012 | Shan | |
| 8,332,035 B2 | 12/2012 | Taizzo et al. | |
| 2004/0172116 A1* | 9/2004 | Seifert ................. | A61N 1/0573 |
| | | | 607/119 |
| 2004/0254534 A1 | 12/2004 | Bjorkman et al. | |
| 2005/0010238 A1* | 1/2005 | Potter ............... | A61M 39/0606 |
| | | | 606/129 |
| 2013/0012824 A1 | 1/2013 | Vanney et al. | |
| 2017/0065267 A1* | 3/2017 | Fantuzzi ........... | A61M 39/0606 |
| 2020/0197088 A1 | 6/2020 | Vrba et al. | |

OTHER PUBLICATIONS

Pressure Products Medical Supplies, Inc., "SafeSheath Sealing Adapter", Feb. 2013, 12 pp., Retrieved from the Internet on Jan. 25, 2023 from URL: https://www.pressure-products.com/Downloads/DFU/SA_DFU.pdf.

Pressure Products Medical Supplies, Inc., "SafeSheath Sealing Adapter: Hemostatic Valve for Medtronic and St. Jude Medical Introducers", 2 pp., Retrieved from the Internet on Jan. 25, 2023 from URL: https://www.pressure-products.com/Downloads/PS/SA_PS.pdf.

International Search Report and Written Opinion of International Application No. PCT/IB2023/060819 dated Jan. 10, 2024, 8 pp.

* cited by examiner

600

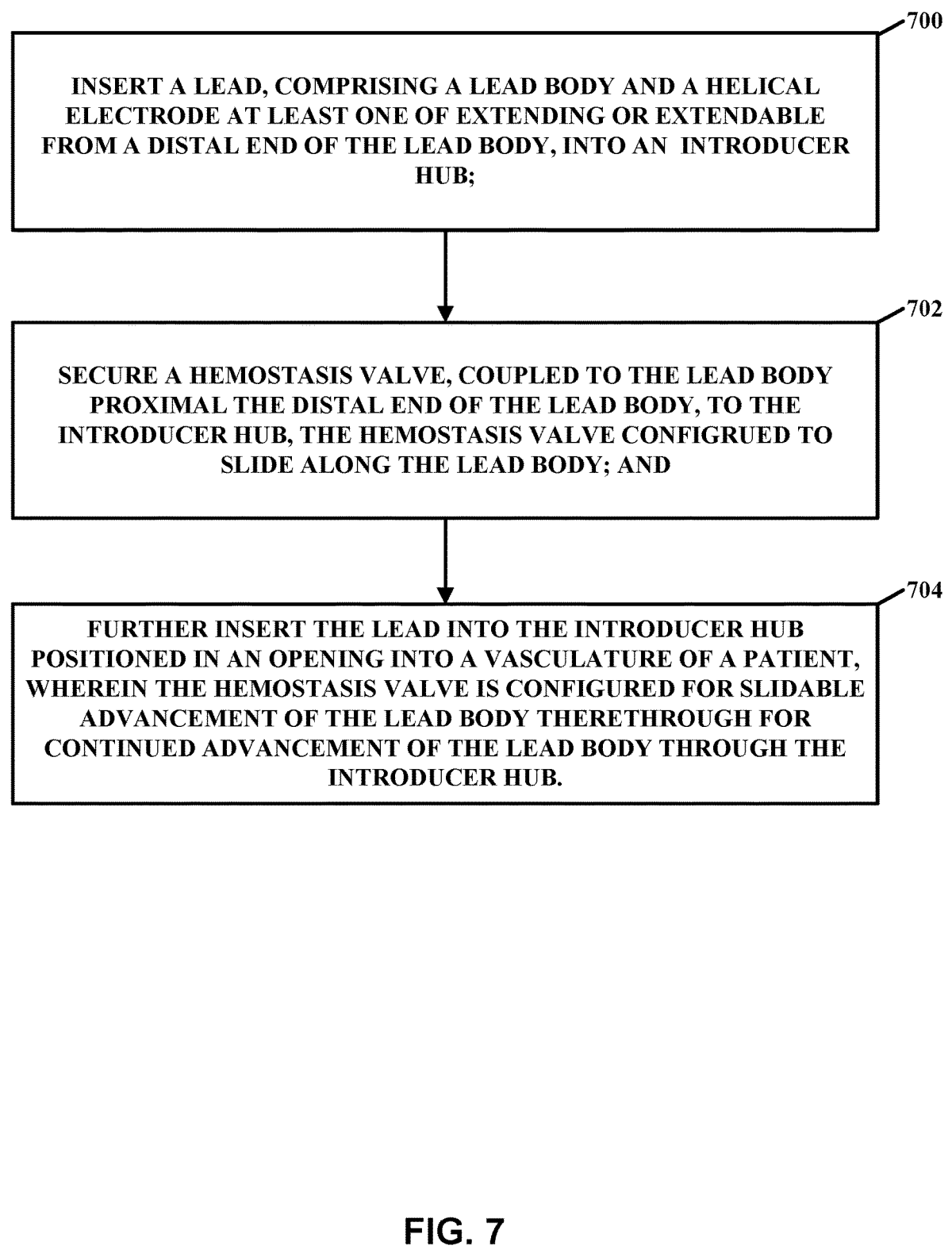

700

INSERT A LEAD, COMPRISING A LEAD BODY AND A HELICAL ELECTRODE AT LEAST ONE OF EXTENDING OR EXTENDABLE FROM A DISTAL END OF THE LEAD BODY, INTO AN INTRODUCER HUB;

702

SECURE A HEMOSTASIS VALVE, COUPLED TO THE LEAD BODY PROXIMAL THE DISTAL END OF THE LEAD BODY, TO THE INTRODUCER HUB, THE HEMOSTASIS VALVE CONFIGRUED TO SLIDE ALONG THE LEAD BODY; AND

704

FURTHER INSERT THE LEAD INTO THE INTRODUCER HUB POSITIONED IN AN OPENING INTO A VASCULATURE OF A PATIENT, WHEREIN THE HEMOSTASIS VALVE IS CONFIGURED FOR SLIDABLE ADVANCEMENT OF THE LEAD BODY THERETHROUGH FOR CONTINUED ADVANCEMENT OF THE LEAD BODY THROUGH THE INTRODUCER HUB.

FIG. 7

SEPARATE POSITIONABLE HEMOSTASIS VALVE FOR IMPLANTABLE MEDICAL LEAD INTRODUCER HUB

TECHNICAL FIELD

This disclosure relates generally to implantable medical leads and, more particularly, to systems for implanting medical leads.

BACKGROUND

Some types of implantable medical devices (IMDs), such as cardiac pacemakers or implantable cardioverter defibrillators systems, may be used to provide cardiac sensing and therapy for a patient via one or more electrodes. Some IMDs include one or more implantable medical electrical leads that include one or more electrodes. Some implantable medical leads may be configured for more temporary use, e.g., for temporary pacing for a matter of months after vascular surgery.

The leads may be introduced into the body through an incision in an artery or vein, and thereafter advanced through the vascular system and, in some cases, into the heart. An introducer, e.g., sheath, may be positioned in the opening to maintain the opening and allow a port of access for the lead. The lead may be advanced through the introducer into the vein or artery and to the cardiac tissue. Implantable medical leads may also be extracted from the vasculature through a sheath positioned in an incision of the artery or vein.

SUMMARY

Introducers may include an integrated hemostasis valve to prevent bleeding during medical lead implantation. However, some leads include components that may be damaged by insertion through a hemostasis valve, such as distal helices or balloons.

In accordance with the techniques of this disclosure, a medical system includes an implantable medical lead and a hemostasis valve that is separate from an introducer hub. The hemostasis valve is slidably disposed on the implantable medical lead proximal the distal end of the lead, e.g., proximal to a distal helix or balloon of the lead. The hemostasis valve may be inserted into a hub of the introducer to provide hemostasis as the implantable lead is inserted through the introducer. In this manner, the lead is introduced, and the hemostasis valve is positioned to provide hemostasis without requiring the distal portion of the lead to be introduced through the hemostasis valve. Thus, the techniques of this disclosure limit the risk of damage to an implantable lead or catheter while lowering the risk of bleeding to the patient during the implantation procedure.

The introducer may be a polymer apparatus formed around a polymer sleeve. The polymer sleeve, or sheath, may have an opening configured to accept a variety of shapes and sizes of hemostasis valve with corresponding implantable medical lead. The introducer hub is further configured for securing the hemostasis valve, allowing the lead body to slide through the valve while maintaining a hemostatic seal. Furthermore, in addition to preventing damage to fragile lead components, the hemostasis valve may provide versatility in its compatibility with different thicknesses of lead body.

In one example, a medical system is disclosed, which includes an implantable medical lead which further includes a lead body and a helical electrode extending or extendable from a distal end of the lead body. The medical system also includes a hemostasis valve coupled to the lead body, the lead body having a proximal end and distal end, and the hemostasis valve being configured to slide along the lead body. The distal end of the lead body may be configured for insertion into an introducer hub positioned in an opening into a vasculature of a patient and the lead body is configured for subsequent advancement through the introducer hub to facilitate securing the hemostasis value to the introducer hub. The hemostasis valve may be configured for slidable advancement of the lead body therethrough for continued advancement of the lead body through the introducer hub.

In another example, a process of using a medical system is disclosed, which includes inserting a lead comprising a lead body and a helical electrode at least one of extending or extendable from a distal end of the lead body. The process also includes coupling a hemostasis valve, coupled to the lead body proximal the distal end of the lead body, to an introducer hub, the hemostasis valve configured to slide along the lead body. In addition, the process includes further inserting the lead into the introducer hub positioned in an opening into a vasculature of a patient. The hemostasis valve is configured for slidable advancement of the lead body therethrough for continued advancement of the lead body through the introducer hub.

In another example, a medical system kit is disclosed, which includes an implantable medical lead comprising a lead body and a helical electrode at least one extending or which is extendable from a distal end of the lead body. The medical system kit also includes a hemostasis valve coupled to the lead body which is proximal the distal end of the lead body, and the hemostasis valve configured to slide along the lead body. The medical system kit also includes a package containing the implantable medical lead with the hemostasis valve coupled thereto. The distal end of the lead body configured for insertion into an introducer hub positioned in an opening into a vasculature of a patient and the lead body configured for subsequent advancement through the introducer hub to facilitate securing the hemostasis valve to the introducer hub. The hemostasis valve is configured for slidable advancement of the lead body therethrough for continued advancement of the lead body through the introducer hub.

In a further example, a process of manufacturing a medical system kit is disclosed, which includes forming an implantable medical lead comprising a lead body and a helical electrode at least one of extending or extendable from a distal end of the lead body. The process includes forming a hemostasis valve configured to slide along the lead body. The process further includes coupling the hemostasis valve to the lead body proximal the distal end of the lead body. Also included in the process is placing the implantable medical lead with the hemostasis valve coupled thereto within a package, wherein the distal end of the lead body is configured for insertion into an introducer hub positioned in an opening into a vasculature of a patient and the lead body configured for subsequent advancement through the introducer hub to facilitate securing the hemostasis valve to the introducer hub. The hemostasis valve is configured for slidable advancement of the lead body through the hemostasis valve for continued advancement of the lead body through the introducer hub.

The details of one or more examples are set forth in the accompanying drawings and the description below. Other features, objects, and advantages will be apparent from the description and drawings, and from the claims.

BRIEF DESCRIPTION OF THE DRAWINGS

FIG. 7 is a flow diagram illustrating an example process of using a hemostasis threaded lead, in accordance with one or more techniques of the disclosure.

DETAILED DESCRIPTION

Figure 1:
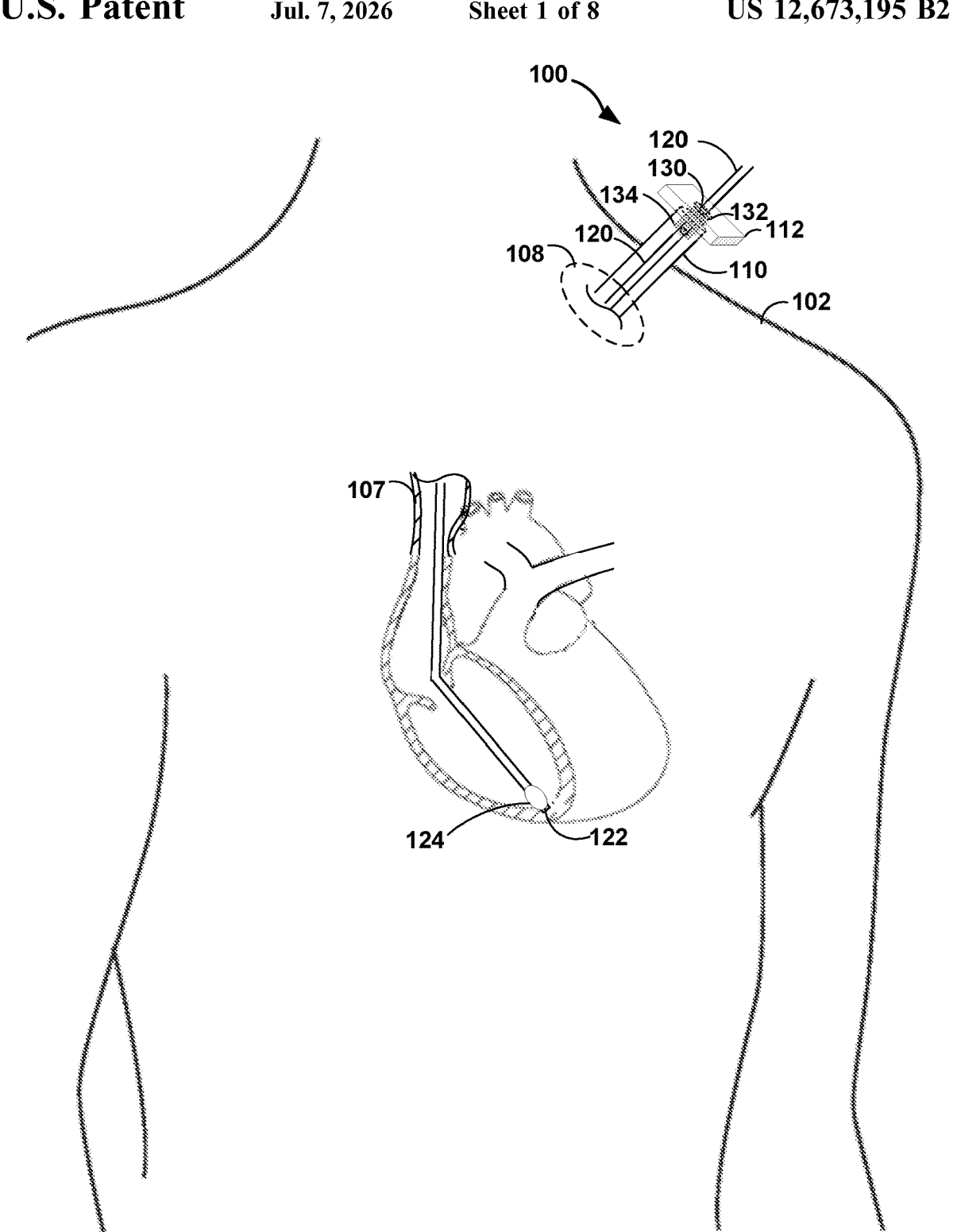
FIG. 1 is a conceptual drawing illustrating an example medical system including an introducer and a separate positionable hemostasis valve for insertion of an implantable medical lead into the vasculature of a patient.

When implanting a lead or other IMD (e.g., a catheter) into the body of a patient, e.g., the vasculature, a clinician may be required to make an incision in the patient to create an access site for implanting the lead. The clinician may then use a variety of tools to prepare the access site for implantation. After preparing the access site, a user may use a variety of tools to introduce the IMD into the vasculature of the patient through the access site.

The user may include a doctor, surgical assistant, medical practitioner, or other qualified medical specialist trained in using the medical tools. One tool the user may use for assisting with the access site, is an introducer. The introducer may assist the user in holding open the access site so that the user may introduce the IMD into the vasculature of a patient. An introducer is a medical tool that may be used to hold the access site open while limiting the risk of injury to the patient, while implanting an IMD into the vasculature of the patient. In particular, the introducer may shield the vasculature from inadvertent puncture while introducing a lead.

The introducer may include a cylindrical sleeve or sheath for feeding into the access site. The introducer may be fed partially into the vasculature of the patient, preventing the vein or artery from closing, while also protecting the vein or artery from injury by the implantable medical lead. An introducer hub may make up a proximate end of the introducer. The introducer hub may be situated on the surface of the patient's body while the distal end of the introducer is fed into the vasculature of the patient. The introducer hub provides a point of entry for the IMD into the introducer and into the vasculature of the patient. Because the introducer is configured to hold open the access site of the vein or artery of the vasculature, bleeding poses a risk. Bleeding may occur when an incision in the vasculature of a patient is held open without impeding the flow of blood out of the incision. To limit the risk of bleeding, the introducer may utilize a hemostatic valve, e.g., integrated at or near the proximal end of introducer hub. The hemostatic valve may be configured to prevent blood from flowing out of the point of entry on the introducer hub.

In some examples, the introducer hub has an introducer hub access point. The introducer hub access point acts as the point of entry for the IMD into the vasculature of the patient. The access point may be an opening in the external end of the introducer hub. The opening may extend through the introducer hub, through the introducer, exiting into the vasculature of the body of the patient. The introducer hub access point may also pose a bleeding risk to the patient. To limit the risk of bleeding from the access point of the introducer hub, while maintaining accessibility for introduction of IMDs, a hemostasis valve may be used.

The hemostasis valve may include a sealing mechanism with an adjustable opening, that fits between the external body surface of the IMD and the access point. One example of a sealing mechanism includes a constrictive gasket. The opening in the hemostasis valve may be configured with a gasket to constrictively seal around the body of IMD. The constrictive gasket may be used to prevent blood from flowing past the hemostasis seal. The constrictive gasket may also be configured to allow the body of the IMD to slide forward or backward, allowing the user to advance or extract an IMD.

In some examples, the hemostasis valve may be positioned in the opening of the introducer hub. The hemostasis valve may be affixed to the introducer hub with a cap, a clip, or another securing mechanism. The hemostasis valve may be configured to allow an IMD to be inserted into a stretchable gasket in the valve when a force is applied. In some examples, the gasket, of the hemostasis valve, may be widened with the applied force from an IMD. If there is no IMD applying a force, the stretchable gasket may constrict, shrinking the size of the stretchable opening, and preventing blood flow. When an IMD is present the opening may seal around the outer surface of the IMD, preventing blood flow around the IMD.

In some examples, the hemostasis valve is first coupled to the introducer hub, e.g., by being integrated with the introducer hub, before being coupled to an IMD. The hemostasis valve may be manufactured with the introducer hub or inserted into the introducer hub during an assembly state.

Integrating an introducer hub with a hemostasis value, before introducing an IMD, is feasible but may limit the user in some respects. In particular, once the user selects an introducer hub with an integrated hemostasis seal, the user may be limited to the size of IMD that may be used with that particular introducer hub and hemostasis valve combination. This limitation may increase the needs of medical facilities to stockpile multiple introducer hub and hemostasis valve combinations. It may also increase the risk that a user may accidently attempt to use an incompatible IMD with a particular introducer hub and hemostasis valve combination. Using an incompatible IMD may cause damage to the hemostasis valve, introducer hub, or IMD, or result in injury to the patient.

Variation in the IMD size, e.g., diameter of the lead body, poses a challenge for selecting a hemostasis valve that properly seals against the IMD. Irregular thicknesses along the IMD body pose challenges for the design and use of a hemostasis valve. A particular IMD may not be compatible with an introducer hub and hemostasis valve combination because, the size of the stretchable opening in the hemostasis valve, may be limited. In some examples, an introducer hub integrated with a hemostasis valve may limit the size of IMD body with which the introducer is compatible. In particular, the diameter of the introducer opening may not accommodate the IMD. However, exclusively increasing the diameter of the introducer opening may pose additional challenges. In one example, an introducer hub integrated with a hemostasis valve, having a wider opening with a similarly narrow hemostasis valve gasket may continue to limit the size of IMD for which the introducer and valve combination is compatible. For example, the gasket opening may be limited by how wide the opening may be expanded or stretched by the IMD, without damage. An IMD including a balloon or other delicate medical attachment, may be damaged by the constrictive force of the hemostasis valve gasket.

In one example, an introducer hub integrated with a hemostasis valve, having a gasket with a wide opening, may be limited by the size in which the opening may constrict, while preventing blood flow. If an IMD with an incompatible narrow body width was selected, the constrictive force on the IMD by the hemostasis valve, may be light, such that a restriction of blood would be small, allowing significant amounts of blood to flow between the valve and the IMD body. With limited constriction and inadequate blood restriction, the use of an incompatible IMD could result in increased hemorrhaging risk to the patient.

In accordance with one or more techniques of this disclosure, some examples of hemostasis valves, methods for using hemostasis valve, hemostasis valve and IMD kits, and methods for assembling hemostasis valves, are presented. Some of these examples illustrate solutions to limitations imposed when inserting an implantable medical lead into the vasculature of a patient. Some examples include separate positionable valves for use on a lead or other IMD. Additional examples include processes for assembling and using leads or other IMDs with separate positionable hemostasis valves. These and other examples are described in accordance with one or more techniques of the disclosure.

FIG. 1 is a conceptual drawing illustrating an example of an implantable medical system 100 in conjunction with a patient 102. System 100 includes an introducer 110, a separate positionable hemostasis valve 134, and an implantable medical lead 120. In some examples, coupling hemostasis valve 134 to lead 120, before introducing the IMD into the introducer hub may be less limiting than integrating the hemostasis valve with the introducer hub, and provide other advantages as described herein.

In the example of FIG. 1 lead 120 is being inserted into vasculature 107 of patient 102. FIG. 1 depicts an access site 108 made by incision in the body of patient 102. An introducer 110 is inserted into access site 108 and fed into vasculature 107 of the patient. Introducer 110 has an opening that aligns with an access point 132 on introducer hub 112. Introducer 110 may be a polymer sleeve, configured to hold access site 108 open for insertion of medical devices, such as implantable medical device leads. Introducer hub 112 is formed from the proximate end of the introducer. Introducer hub 112 may have access point 132 that includes a rigid opening made of polymer or other firm material. Access point 132 may be configured to accept lead 120. In some examples the implantable medical lead may be fed through the access point 132 of introducer hub 112 and into the opening of introducer 110.

To prevent blood flow through the potential gap between the body of lead 120 and the opening of introducer 110, and out of access point 132, a hemostasis valve 134 may be used. In some examples hemostasis valve 134 is positioned in introducer hub 112. Hemostasis valve 134 may be configured to fill access point 132. Filling access point 132 may prevent hemorrhaging when the introducer has been fed into vasculature 107 of patient 102. In some examples, the exterior surface of the IMD lead body may form a seal with the inner surface of introducer hub assess point 132. The seal may be formed from the expansionary nature of the material used to make hemostasis valve 134. In some examples, friction force between the outer surface of the hemostasis valve and the inner surface of the introducer opening may prevent the flow of blood from expelling hemostasis valve 130 from introducer hub 112.

In some examples, hemostasis valve access point 130 may be stretchable and configured to constrict around the body of lead 120. Hemostasis valve access point 130 may be stretchable up to the cross-section width of the access site 132 of the introducer hub. In some examples, the widest cross-section of the implantable medical lead may be narrower than the maximum width to which hemostasis valve access point 130 may be stretched. In one example, the limit may be due to the rigid nature of the access site, in which hemostasis valve 134 is disposed. In some examples, hemostasis valve access site 130 may be stretched wider, without damage to hemostasis valve 134, if hemostasis valve was not restricted by rigid properties of accesses point 132. The constrictive feature of the hemostasis valve access point 130 may form a slidable seal around the body of IMD lead 120. In some examples, the constrictive feature of hemostasis valve 134 may be due to an elastomeric property of the material comprising the hemostasis valve. The constrictive feature may also limit the size to which the hemostasis valve access point 130 may be widened.

Lead 120 may be a temporary pacing lead. In some examples, as shown in the example of FIG. 1, lead 120 may include a balloon 124 near distal tip 122. Because balloon 124 is small yet inflatable, the polymer material used in the balloon may be very thin and easily ripped. For this and other reasons, balloon 124 could be damaged if inserted through a constricted opening 130 of hemostasis valve 134. Additionally, although not illustrated in FIG. 1, lead 120 may include a helix, tine(s), or other fixation mechanism extending or extendable from distal end 122 of lead 120. Particularly when fixedly extending from distal end 122, such fixation mechanisms could be damaged or cause damage when advanced through opening 130 of hemostasis valve 134.

Medical system 100 is an example of a medical system configured to avoid such issues by implementing the techniques of this disclosure. In particular, hemostasis valve 134 is coupled to, e.g., positioned or disposed on, lead 120 prior to insertion of lead 120 into introducer 110 via access point 132 of introducer hub 112. Hemostasis valve 134 is positioned on lead 120 proximal of distal end 122 of lead 120, e.g., the lead body. Hemostasis valve 134 is configured to slide along lead body 120. With lead 120 inserted into introducer 110 via access point 132, hemostasis valve 134 may be advanced into access point of introducer hub 112 and secured to the introducer hub 112, e.g., in the configuration shown in FIG. 1. Hemostasis valve 134 is configured to provide hemostasis as lead 120 is further advanced through the hemostasis valve and introducer 110.

Figure 2:
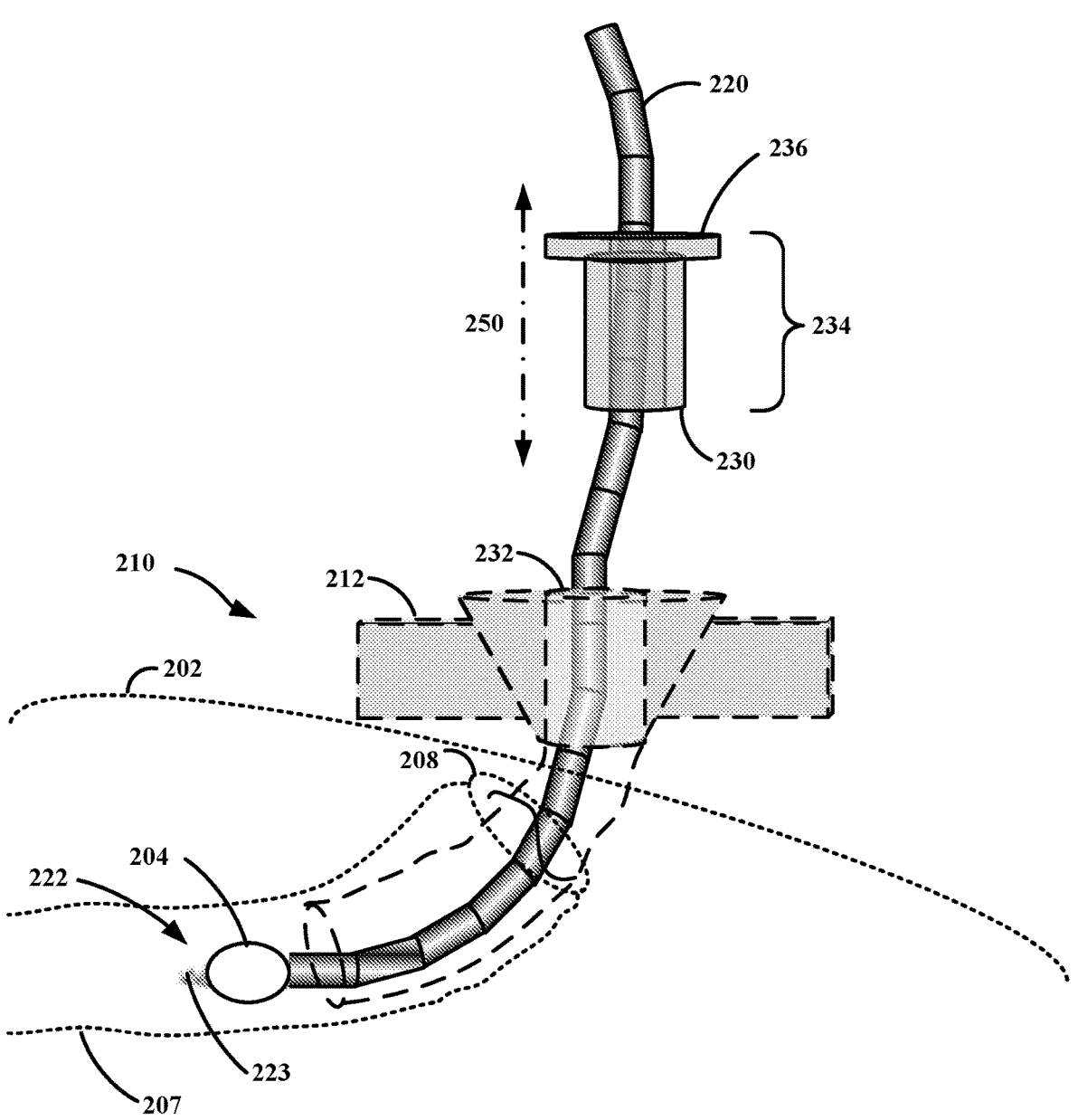
FIG. 2 is a conceptual drawing illustrating a closeup view of an example hemostasis valve coupled to an implantable medical lead being inserted through an in introducer into the vasculature of a patient, in accordance with one or more techniques of the disclosure.

FIG. 2 is a conceptual diagram illustrating a closeup view of a separate positionable hemostasis valve 234 coupled to an implantable medical lead 220 for insertion into an introducer 210, in accordance with one or more techniques of the disclosure. The conceptual diagram of FIG. 2 is not to scale, and a hemostasis valve 234 may be much smaller than introducer 210 in FIG. 2. Hemostasis valve 234 may be coupled to the body of lead 220 before being coupled to introducer 210. Hemostasis valve 234 may be configured to slide along the external surface of the body of lead 220, e.g., as illustrated by arrow 250.

In some examples, hemostasis valve 234 may be formed onto or positioned on the body of lead 220 proximal a distal end 222 of the body of lead 220, e.g., before packaging of lead 220 for eventual sale/use. As illustrated in FIG. 2, lead 220 may include a helix 223 that acts as a fixation element and/or electrode extending or extendable from distal end 222 of the body of lead 220. Lead 220 may also include an expandable balloon 204 on the distal portion of the lead body near to and proximal of helix 223. Balloon 204 may be expanded during a procedure to implant lead 220, e.g., upon or shortly after distal end 222 exits the distal end introducer 210 into vasculature 207 of patient 202, to protect the vasculature from helix 223. In some examples, balloon 204 expands to at least partially surround helix 223. In some examples, the flow of blood may apply a force to lead 210 via balloon 204 to guide lead 210 towards a target implant location. To avoid advancing helix 223 and balloon 204 through hemostasis valve 234, hemostasis valve 234 may be coupled to the body of lead 210 proximal of the helix and the balloon prior to a procedure to implant lead 210.

In some examples, the process step of forming the hemostasis valve 234 circumferentially around the lead body may cause it to slidably couple to exterior surface of the IMD lead body. In some other examples, an additional step may need to be performed to couple/position hemostasis valve 234 to the body of lead 220.

In some examples, as an assembly step, hemostasis valve 234 may be stretched to fit around the body of lead 220, e.g., to allow helix 223 and balloon 204 to pass therethrough without damage. In particular, a hemostasis valve access point in a gasket may be widened to accommodate feeding the distal end of the IMD lead into the hemostasis valve access point. Releasing the hemostasis valve access point may cause the hemostasis valve to slidably couple to the body of the IMD lead body. In some cases, the coupling allows hemostasis valve 234 to slide along IMD lead body 220. In some examples, as an assembly step, distal end 222 of the body of lead 210 may be advanced through hemostasis valve 234, e.g., a gasket thereof, prior to attaching or forming helix 223 and/or balloon 204 on lead 220.

During implantation of lead 220, distal end 222 may be fed into access point 232 of the introducer 210 with hemostasis valve 234 slidably coupled to the body of lead 220 proximal the distal end. The body of lead 220 may slide through introducer 210. IMD lead 220 may be fed into introducer 210 with hemostasis valve 234 coupled to the body of IMD lead 220. In some examples, lead 220 may be fed into vasculature 207 of patient 202 up to a coupling point, where hemostasis valve 234 couples to lead 220. In some examples, hemostasis valve 234 may additionally or alternatively be advanced along the body of lead 220 to introducer 210.

In some examples, a distal end 230 of hemostasis valve 234 may be inserted into access point 232 in a hub 212 of introducer 210. Hemostasis valve 234 may be press fit into access point 232. The press fit may occur by feeding distal end 230 of hemostasis valve 234 into access point 232 up to a point when a proximal end 236 of the hemostasis valve 234 is flush with a proximal end of introducer 210, e.g., the proximal end of hub 212.

In some examples, hemostasis valve 234 is configured to create a seal between the inner surface of assess point 230 and the external surface of the body of lead 220. In some examples, the seal is produced by the tapered design of the hemostasis valve 234. In particular, a tapered structure of hemostasis valve 234 exists when a difference in width exists between proximal end 236 and distal end 230 of hemostasis valve 234. In such an example, proximal end 236 is configured to have a cross-sectional diameter greater than a cross-sectional diameter of distal end 230. A difference in cross-sectional diameters creates a radial narrowing of the width along the length of the hemostasis valve from proximal end 236 to distal end 230. Proximal end 236 may be larger than opening 232 in the introducer hub while the distal end 208 is narrower than the opening 232. In some examples the width of the external surface of the hemostasis valve 234 tapers down from the proximal end 236 to the distal end 230.

In some examples, a press-fit connection may be formed with hemostasis valve 234 designed to narrow in width from proximal end 236 to distal end 230 with discrete steps. In some examples the discrete steps may form a ledge or stop those presses against the introducer 210, when hemostasis valve 234 is secured to introducer.

Hemostasis valve 234 may comprise a variety of materials. Some material may include a variety of polymers, elastomeric foams, or other malleable materials. The malleable nature of the material used in the hemostasis valve may allow the hemostasis valve to create a friction enforced seal between hemostasis valve 234 and introducer hub 210. The malleable nature of the material may also determine the ease with which the valve is able to slide along the body of lead 220.

In one example of FIG. 2, access point 232 of introducer hub 212 may be sized to accommodate a variety of distal ends 222. In particular, access point 232 may be wide enough to allow the passage of balloon 204. Balloon 204 may be configured to a variety of different sizes. Access point 232 may be sized to accommodate a variety of elements used on the distal tip of the lead. In some examples, the width of the exterior surface of hemostasis valve 234 may be configured to fit access point 232 of the introducer hub 212. In some examples, the width of the exterior surface may be wider than the opening 232 of the introducer hub 212 but configured to compress to a size that fits into opening 232.

In the example of FIG. 2, proximal end 236 of hemostasis valve 234 has an enlarged portion. The enlarged portion may be configured to exceed the width of access point 232. The enlarged portion may create a stop or break against a proximal surface of introducer 210, e.g., of introducer hub 212. In some examples, a latch or locking mechanism on the introducer hub 210 may be configured to hold or lock the enlarged portion of the hemostasis valve 234 to the introducer hub 210.

Figure 3:
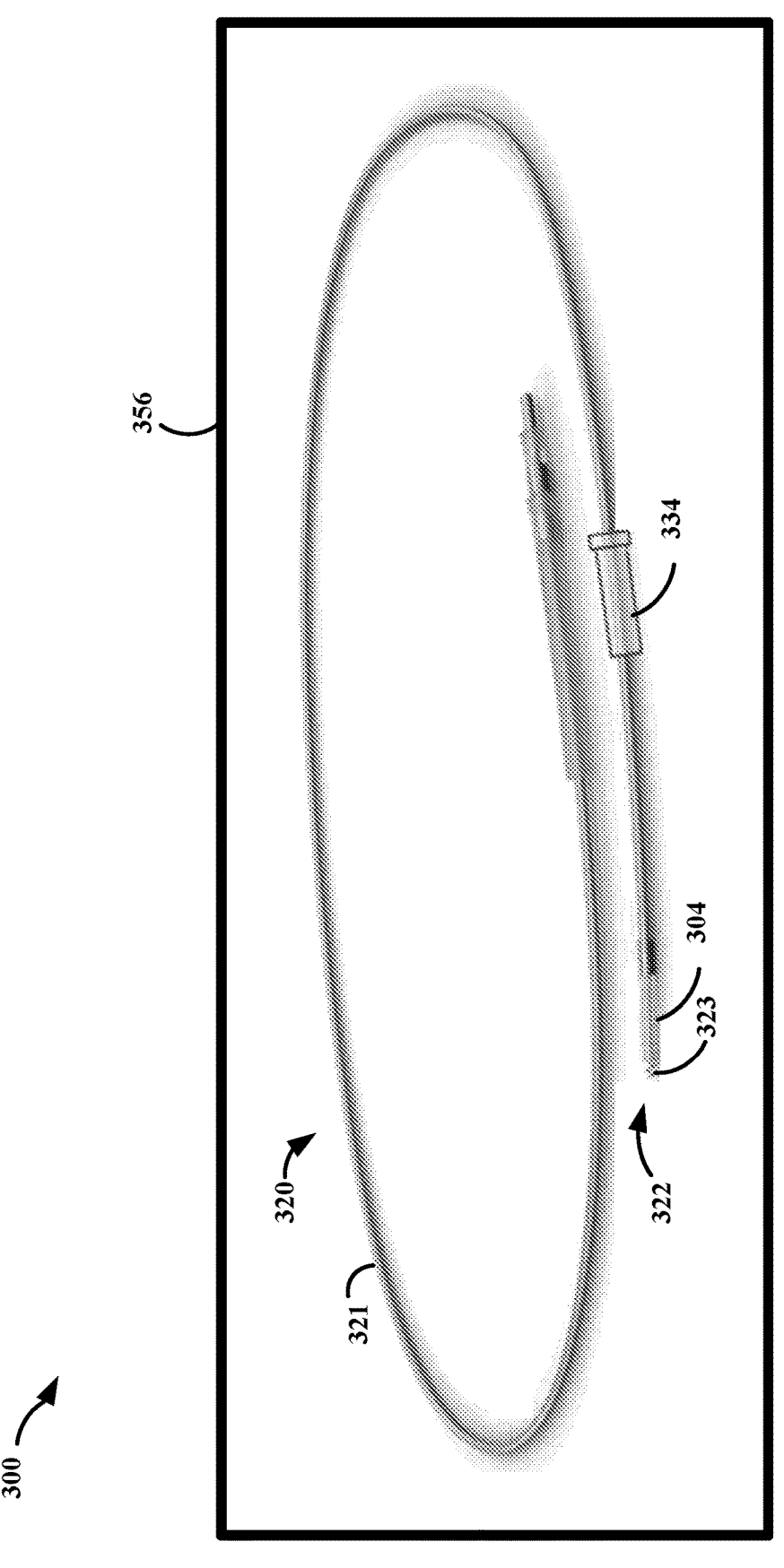
FIG. 3 is a conceptual drawing illustrating an example of a medical system kit including an introducer and a separate positionable hemostasis valve within a package.

FIG. 3 is a conceptual diagram illustrating an example of a kit 300 including a separate positional hemostasis valve 334 coupled to an implantable medical lead 320, in accordance with one or more techniques of the disclosure. In some examples the hemostasis threaded lead may be manufactured with the hemostasis valve 334 coupled to the body 321 of lead 320 proximal to a distal end 322 of lead 320, e.g., positioned as shown in FIG. 3. In some examples, kit 300 includes lead 320 with separate positionable hemostasis valve 334 in a package 356, e.g., a sterile package intended to be opened for a procedure to implant lead 320 in a patient.

In some examples, lead 320 may comprise a balloon 304 near distal end 322, e.g., as described above with respect to balloon 104 of FIG. 1 and balloon 204 of FIG. 2. Balloon 304 may be positioned proximal of e.g., right above, distal end 322 of lead body 321. Distal end 322 may include an exposed stimulation electrode 323. Some stimulation electrodes may include a helix, a double helix, a coaxial tip, or another conductive tip configured to stimulate muscle tissue.

In the example of FIG. 3, hemostasis valve 334 may be configured to slide along outer body 321 of lead 320. The hemostasis valve may be configured to implement a hemostatic seal between hemostasis valve 334 and outer body 321. Hemostasis valve 334 may be configured to slide along the outer body with some resistance. The resistance may provide a stop or break along lead body 321. Hemostasis valve 334 may be configured to have a consistent resistance between the lead body and the hemostasis valve. The resistance may be similar between a variety of separate positionable hemostasis valves matched with a variety of IMD leads.

In one example of FIG. 3, the hemostasis valve 334 may be sized and selected for a given thickness or profile of lead body. A hemostasis valve configured for a wider lead body may have a wider access point for receiving the medical implantable lead. A hemostasis valve configured for a narrower lead body may have a narrower access point for providing an appropriately tight hemostatic seal against the outer body of the implantable medical lead.

Figure 4:
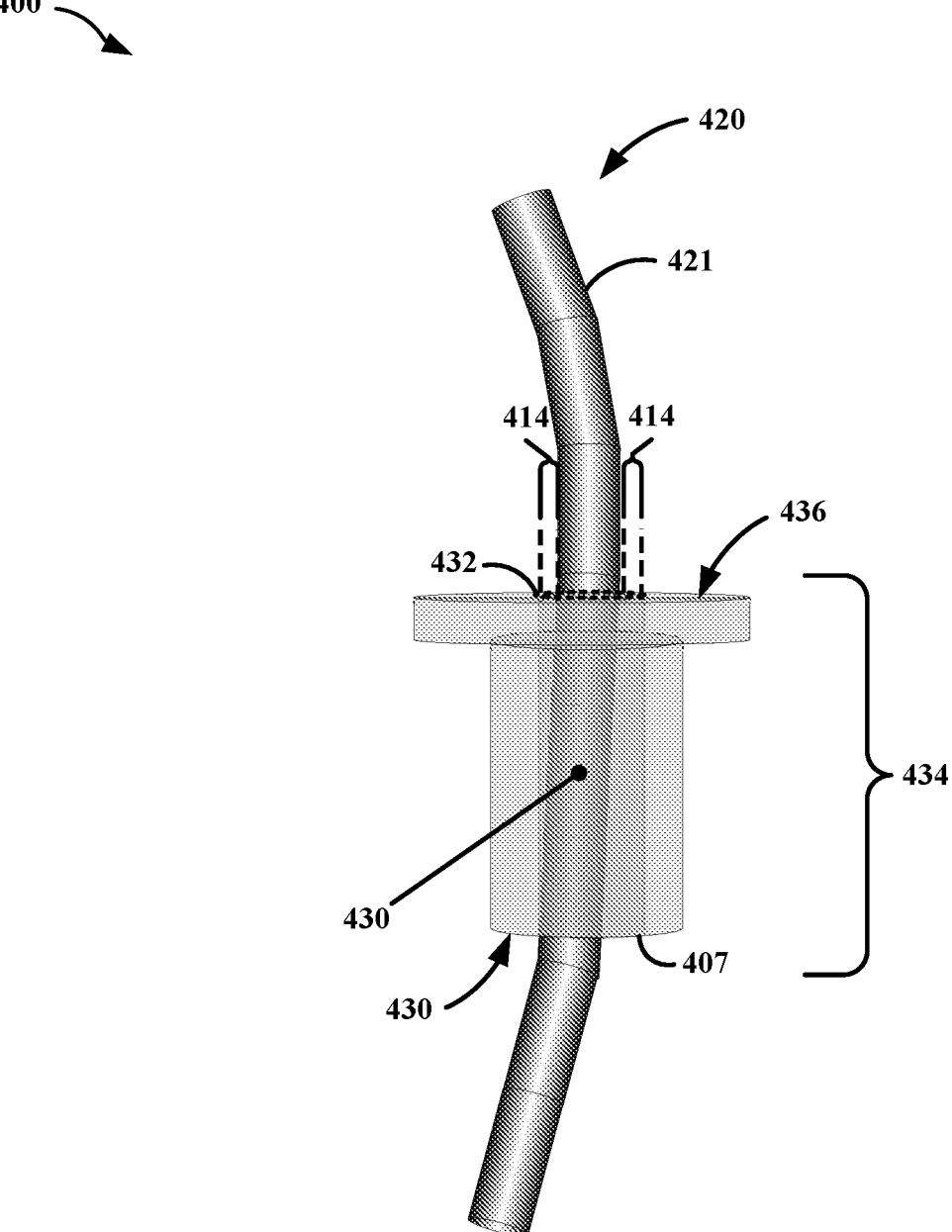
FIG. 4 is a conceptual drawing illustrating another example of a separate positionable hemostasis valve coupled to an implantable medical lead body, in accordance with one or more techniques of the disclosure.

FIG. 4 is a conceptual diagram illustrating an example system 400 including a hemostasis valve 434 coupled to a body 421 of a lead 420, in accordance with one or more techniques of the disclosure. Hemostasis valve 434 may be coupled to body 421 at a coupling point 430. Hemostasis valve 434 may be configured to slide along the outer surface of body 421 or, stated differently, body 421 may be configured to slide through an opening of hemostasis valve 434. Some examples of the slidable configuration include a gap 414 between body 421 and access point 432 of hemostasis valve 434. Gap 414 may allow hemostasis valve 434 to move along the length of body 421 of lead 420. Gap 414 may be configured to inhibit the flow of blood out of the body via hemostasis valve access point 432, while still allowing the hemostasis valve 434 to slide along body 421.

In some examples, hemostasis valve 434 may comprise a variety of materials. Some examples of materials include plastic, rubber, silicone, polymer foam, nylon, or other synthetic material which are malleable under pressure. The malleable nature of the material may allow hemostasis valve 434 to form a hemostatic seal with the access point of an introducer hub. The malleable material may also inhibit the flow of blood out of the body through gap 414 when the hemostasis valve 434 has been secured to the introducer hub.

In some examples the malleable nature of the material of the hemostasis valve may cause distal opening 407 to bend. In some examples, bends in the opening 407 may prevent a path for blood to flow from the distal end 430 of the hemostasis valve 434 to the proximal end 436 of the hemostasis valve. However, the bend in the opening 407 may reduce the surface area where the IMD lead contacts the hemostasis valve, allowing the IMD lead body to slide through opening 407.

Figure 5:
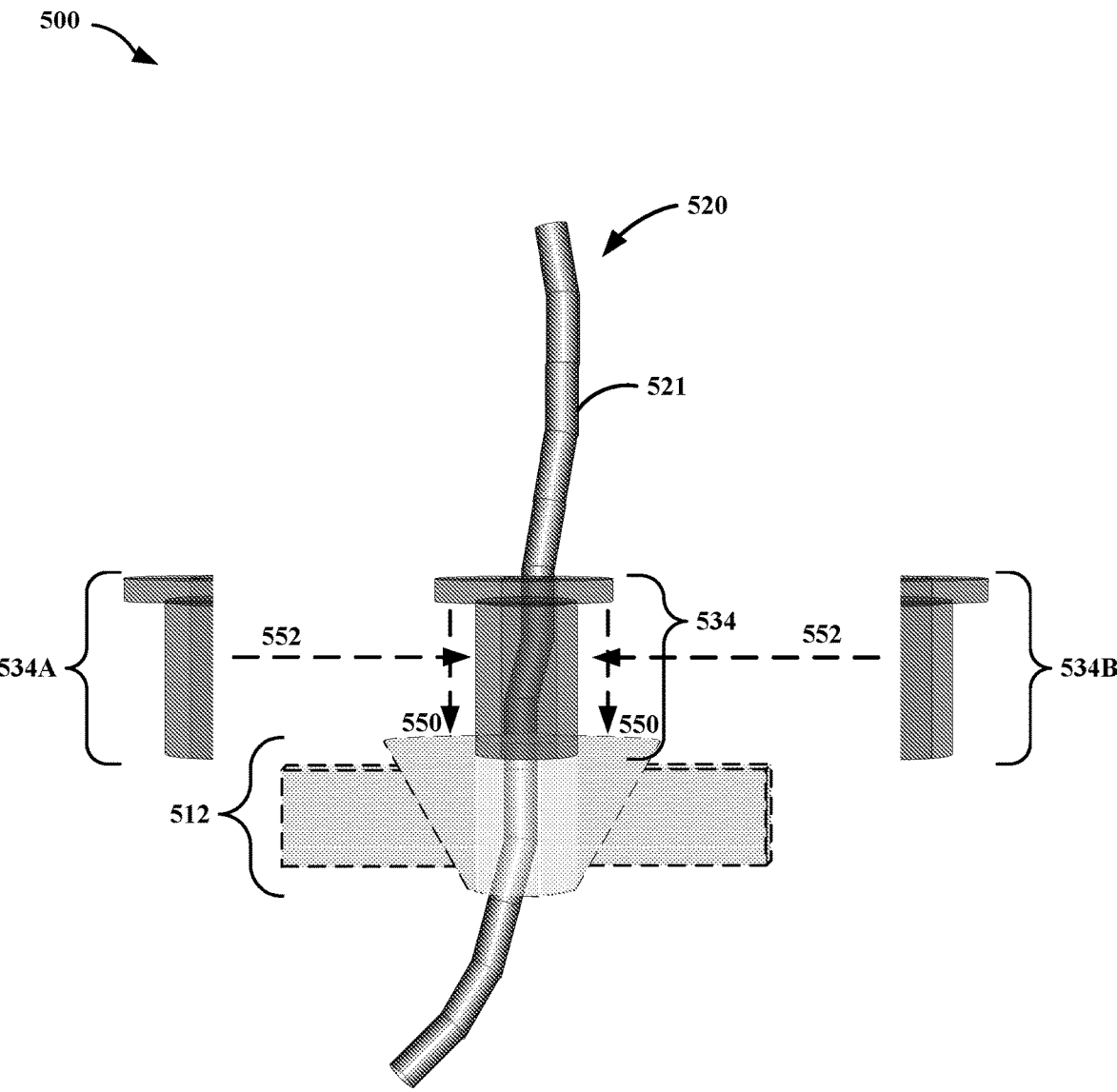
FIG. 5 is a conceptual drawing illustrating an example of forming a separate positionable hemostatic valve and coupling the valve to the implantable medical lead and introducer, in accordance with one or more techniques of the disclosure.

FIG. 5 is a conceptual diagram illustrating the formation of a hemostasis valve 534 onto a body 521 of an implantable medical implantable lead 520 and the insertion 550 into an introducer hub 512 of an introducer, in accordance with one or more techniques of the disclosure. In some examples hemostasis valve 534 may be formed onto body 521, prior to coupling the hemostasis valve to introducer hub 512. Hemostasis valve 534 may be formed from two or more pieces, e.g., pieces 534A and 534B, coupled together circumferentially around body 521, e.g., as illustrated by arrows 552. In some examples, the pieces may connect in a variety of ways. Some mechanisms for connecting the pieces may include press-fit, snap, adhesive, or reactive polymer.

In some examples, hemostasis valve 534 may be molded circumferentially around the external surface of body 521 of lead 520. Some examples of the molding process may include extrusion molding, polymer curing, additive manufacturing, multiple element epoxies, or heat activation. In some examples, the molded hemostasis valve may have the same properties as the hemostasis valve described in FIG. 1. In some examples, the molding of the hemostasis valve may be altered depending on the width of the lead body 521. A wider lead body may result in a thinner hemostasis valve and a narrower lead body may result in a thicker hemostasis valve. In some examples, a thinner hemostasis valve may be created by using a thinner layer of material when forming the valve. Similarly, a thicker hemostasis valve may be created by using a thicker layer of material when forming the valve. In some examples, a jig or mold may be used to limit and form the exterior surface and shape of the mold. Such a jig or mold will improve the likelihood of a compatible connection with the opening of the introducer hub.

Once formed around the external surface of body 521, hemostasis valve 534 may slide into an opening of a introducer hub 512 as shown by arrows 550. Hemostasis valve 534 may be secured to introducer hub 512 by a variety of locking mechanisms. Some examples of locking mechanisms for securing the hemostasis valve include a press fit connection, an adhesive connection, a threaded connection, and a snap fit connection.

In some examples, hemostasis valves as described herein may be configured to split. A splitable hemostasis valve may be compatible with a splitable introducer and introducer hub. A splitable hemostasis valve, splitable introducer hub, and splitable introducer may be used to facilitate the quick extraction of the introducer and valve during implantation of the lead, e.g., without requiring these tools to be pulled back over a potentially larger proximal connector portion of the lead. Splitting the introducer hub, introducer, and hemostasis valve along a seam allows the user to quickly remove the medical tools away from the implantable medical lead.

In some examples, a splitable hemostasis valve may be created by adding a line or seam along the length of the hemostasis valve. The line or seam may be perforated, indented, compress, or weakened in some was so as to easily tear when tension forces are applied radially to the hemostasis valve. The line or seam used for splitting the hemostasis valve, may align with a splitable line or seam on the introducer hub and introducer. In some examples the hemostasis valve may split into separate sections with the introducer hub. In some examples the sections may be halves or quarters. A splitable hub and introducer valve allows for quick removal of the introducer hub and introducer from the implantable medical lead. The hemostasis valve and introducer may be splitable in a variety of ways.

Figure 6:
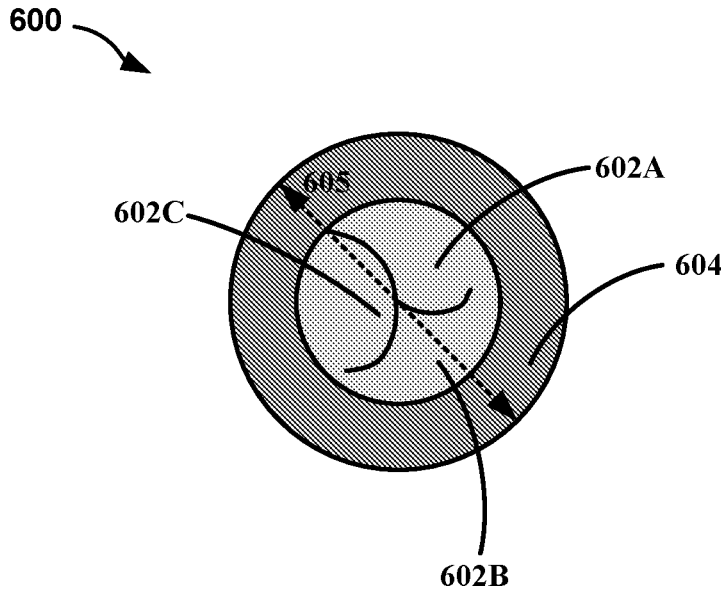
FIG. 6 is a conceptual block diagram illustrating an example process for using a separate positionable hemostasis valve to impede the flow of blood while inserting an implantable medical lead through an introducer into the vasculature of a patient, in accordance with one or more techniques of the disclosure.

FIG. 6 is a conceptual diagram illustrating a perspective view of a hemostasis valve 600, in accordance with one or more techniques of the disclosure. Hemostasis valve 600 may be a cylindrical sleeve with an outer diameter 605. Outer diameter 605 may fit into a cylindrical opening of an introducer hub. Outer diameter 605 may form a hemostatic seal between the introducer hub and the hemostasis valve.

In the example of FIG. 6, an opening of hemostasis valve 600 may be formed with a plurality of leaflets 602A-C. Leaflets 602A-C may be flaps or cusps of medical grade polymer. Some examples of medical grade polymers include polycarbonate, polypropylene, polyethylene, nylon, or other plastic material compatible with biological tissue. Leaflets 602A-C may be configured to bend in one direction but provide resistance to bending in the opposite direction. The resistance to bend may prevent the flow of blood that may cause hemorrhaging during the implantation of medical leads.

In the example of FIG. 6, leaflets 602A-C may tightly seal against the outer body of a implantable medical lead. Leaflets 602A-C may bend to fit the contours of the varying widths of the external body of the implantable medical lead. Leaflets 602A-C may form a malleable contractive opening configured to seal around the outer body of an implantable medical lead. The opening in the hemostasis valve may vary with the contour of the lead body as the implantable medical leads is inserted or retracted from the hemostasis valve.

FIG. 7 is a flow chart illustrating an example of a process of using a hemostasis valve slidably coupled to an implantable medical lead, in accordance with one or more techniques of the disclosure. Some examples of processes of using a hemostasis valve may first include coupling the hemostasis valve to the body of the lead. This may be a step performed by a manufacturer or assembler prior to packaging the system including the hemostasis valve and lead. In some examples, a user may couple the hemostasis valve to the lead.

In the example of FIG. 7, the user, e.g., cardiologist or other clinician, may insert the implantable medical lead into an introducer hub, the introducer hub being coupled to an introducer (700). Introducer may include any medical implantable sleeve coupled to introducer hub that facilitates the advancement of the lead into the vasculature of the patient.

In the example of FIG. 7, the user may then secure the hemostasis valve, slidably coupled to the lead body, to the introducer hub (704). In some examples, securing the hemostasis valve to the introducer hub 706 may be performed with a securing mechanism. Securing mechanism may include a latch or clip or other locking feature. The user may then advance the lead body through the hemostasis valve and, thereby, through the introducer (706).

The hemostasis valve may be any one of hemostasis valves 134, 234, 334, 434, 534, and 600 of FIG. 1-FIG. 6. In some examples, the hemostasis valve may be one formed from multiple pieces or one that is formed or molded around the body of the implantable medical lead. In some examples, the hemostasis valve being configured to slide may be configured to slide as illustrated with a gap 414 of FIG. 4

Figure 8:
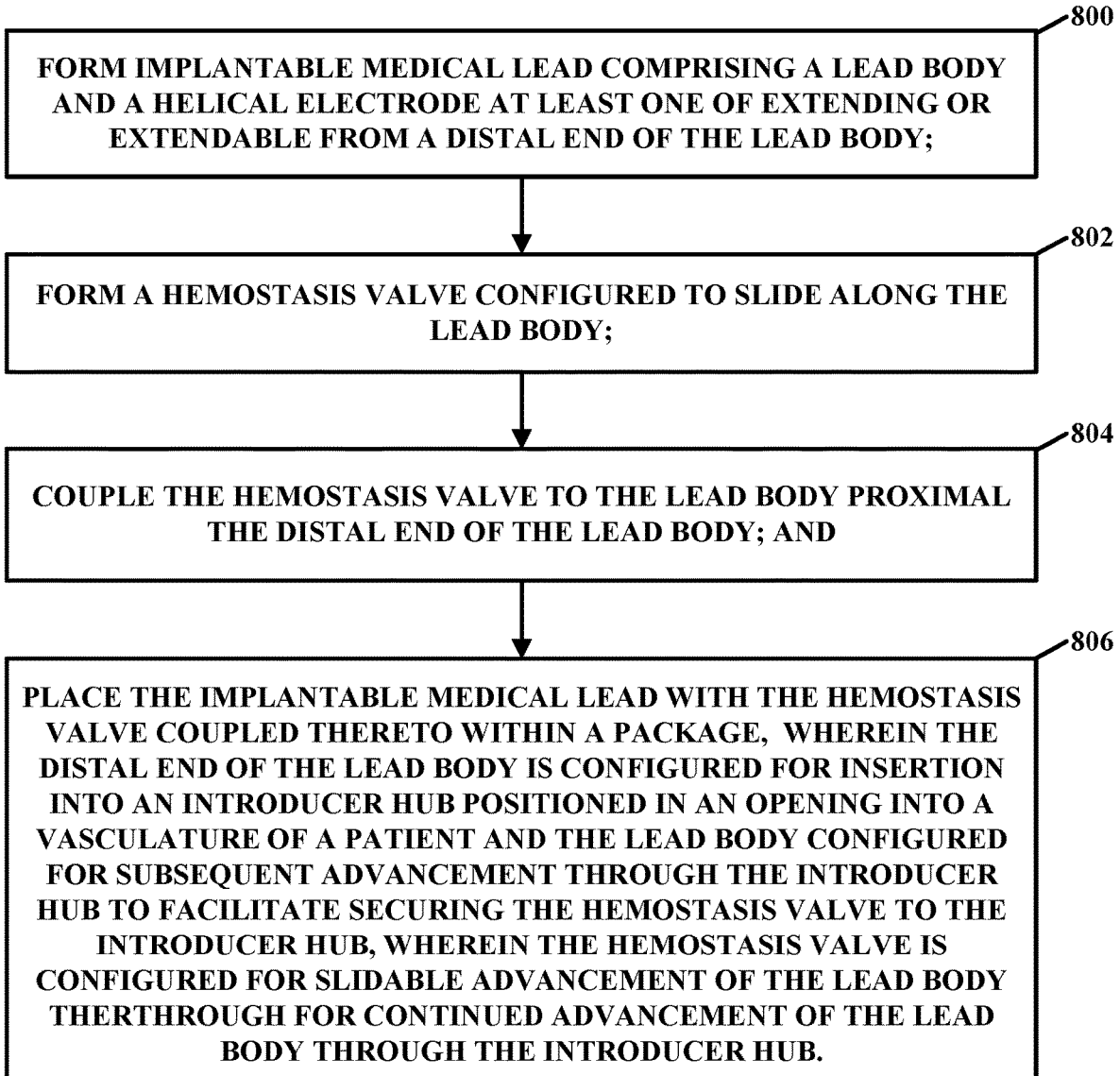
FIG. 8 is a flow diagram illustrating an example process of making a hemostasis threaded lead, in accordance with one or more techniques of the disclosure.

FIG. 8 is a conceptual flow chart illustrating an example of a process of manufacturing a separate positionable hemostasis valve for implantable medical lead introducer hub, in accordance with one or more techniques of the disclosure. In the process, a manufacturer may form implantable medical lead comprising a lead body and a helical electrode at least one of extending or extendable from a distal end of the lead body (800). To form the implantable medical lead may include manufacturing a length of lead. The implantable medical lead formed herein may include any one of implantable medical leads 120, 220, 320, 420, or 520, of respective FIG. 1-FIG. 5.

The example of FIG. 8 may also include a manufacturing step to form a hemostasis valve configured to slide along the lead body (802). Formation may include molding, printing, curing, or other formation process resulting in a hemostasis valve that circumferentially encompasses a portion of the implantable medical lead body. In some examples, a jig, a form, or a mold may be used to align or frame the formed hemostatic valve. The hemostasis valve formed from herein may include any one of hemostasis valves 134, 234, 334, 434, 534, or 600 of respective FIG. 1-FIG. 6.

The example of FIG. 8 may also include a manufacturing step to couple the hemostasis valve to the lead body proximal the distal end of the lead body (804). Coupling may include curing, sticking, pressing, or any other means of temporarily fixing the hemostasis valve to the body of the lead. In some examples, to couple the hemostasis valve to the lead body may include stretching a constrictive gasket around the lead body. In some examples, to couple the hemostasis valve to the lead body may include inserting the lead through the hemostasis valve prior to including a helical electrode, balloon, or other component on the lead, or otherwise prior to finalizing the lead.

The example of FIG. 8 may also include a manufacturing step to place the implantable medical lead with the hemostasis valve coupled thereto within a package (806). The distal end of the lead body is configured for insertion into an introducer hub positioned in an opening into a vasculature of a patient and the lead body configured for subsequent advancement through the introducer hub to facilitate securing the hemostasis valve to the introducer hub, wherein the hemostasis valve is configured for slidable advancement of the lead body therethrough for continued advancement of the lead body through the introducer hub.

This disclosure includes the following non-limiting examples.

Example 1. A medical system comprising: an implantable medical lead comprising a lead body and a helical electrode at least one of extending or extendable from a distal end of the lead body; and a hemostasis valve coupled to the lead body proximal the distal end of the lead body, the hemostasis valve configured to slide along the lead body, wherein the distal end of the lead body is configured for insertion into an introducer hub positioned in an opening into a vasculature of a patient and the lead body configured for subsequent advancement through the introducer hub to facilitate securing the hemostasis value to the introducer hub, wherein the hemostasis valve is configured for slidable advancement of the lead body therethrough for continued advancement of the lead body through the introducer hub.

Example 2. The medical system of example 1, wherein the hemostasis valve extends from a proximal end to a distal end configured for insertion into an opening in the introducer hub, wherein a cross-sectional dimension of the hemostasis valve is tapered from a larger value at the proximal end to a smaller value at the distal end.

Example 3. The medical system of example 2, wherein the cross-sectional dimension of the proximal end of the hemostasis valve is larger than a corresponding dimension of the opening of the introducer hub.

Example 4. The medical system of examples 1-3, wherein the hemostasis valve further comprises: a constricted gasket configured to resist blood flow between the gasket and the lead body when coupled to the lead body.

Example 5. The medical system of example 4, wherein the constricted gasket comprises silicone rubber.

Example 6. The medical system of examples 4-5, wherein the constricted gasket is configured to slide along the lead body, wherein the constricted gasket maintains a hemostatic seal between the lead body and the hemostatic valve.

Example 7. The medical system of example 6, wherein the inner seal comprises leaflets configured to create the hemostatic seal.

Example 8. The medical system of examples 1-7, wherein the implantable medical lead further comprises a balloon proximal of the distal end of the lead body, wherein the hemostasis valve is coupled to the lead body proximal of the balloon.

Example 9. A method of using a medical system comprising: inserting a lead comprising a lead body and a helical electrode at least one of extending or extendable from a distal end of the lead body; and securing a hemostasis valve, coupled to the lead body proximal the distal end of the lead body, to an introducer hub, the hemostasis valve configured to slide along the lead body; an further inserting the lead into the introducer hub positioned in an opening into a vasculature of a patient, wherein the hemostasis valve is configured for slidable advancement of the lead body therethrough for continued advancement of the lead body through the introducer hub.

Example 10. The method of example 9, wherein securing a hemostasis valve further comprises inserting the hemostasis valve, extending from a proximal end to a distal end, into an opening in the introducer hub, wherein a cross-sectional dimension of the hemostasis valve is tapered from a larger value at the proximal end to a smaller value at the distal end.

Example 11. The method of example 10, wherein inserting the hemostasis valve is stopped by the cross-sectional dimension of the proximal end being larger than a corresponding dimension of the opening of the introducer hub.

Example 12. The method of examples 9-11, wherein securing the hemostasis valve further comprises: constricting a gasket of the hemostasis valve around the lead body, thereby configuring the hemostasis vale to resist blood flow between the gasket and the lead body.

Example 13. The method of examples 9-12, wherein further inserting the lead further comprises: sliding an inner seal along the lead body, wherein the inner seal is configured to create a hemostatic seal between the lead body and the hemostatic valve.

Example 14. The method of example 13, wherein sliding an inner seal does not disrupt the hemostatic seal between the gasket and the lead body.

Example 15. A medical system kit comprising: an implantable medical lead comprising a lead body and a helical electrode at least one of extending or extendable from a distal end of the lead body; a hemostasis valve coupled to the lead body proximal the distal end of the lead body, the hemostasis valve configured to slide along the lead body; and a package containing the implantable medical lead with the hemostasis valve coupled thereto, wherein the distal end of the lead body is configured for insertion into an introducer hub positioned in an opening into a vasculature of a patient and the lead body configured for subsequent advancement through the introducer hub to facilitate securing the hemostasis valve to the introducer hub, wherein the hemostasis valve is configured for slidable advancement of the lead body therethrough for continued advancement of the lead body through the introducer hub.

Example 16. The medical system kit of example 15, wherein the hemostasis valve extends from a proximal end to a distal end configured for insertion into an opening in the introducer hub, wherein a cross-sectional dimension of the hemostasis valve is tapered from a larger value at the proximal end to a smaller value at the distal end.

Example 17. The medical system kit of examples 15-16, wherein the cross-sectional dimension of the proximal end is larger than a corresponding dimension of the opening of the introducer hub.

Example 18. The medical system of examples 15-17, wherein the hemostasis valve further comprises: a constricted gasket configured to resist blood flow between the gasket and the lead body when coupled to the lead body.

Example 19. The medical system kit of example 18, wherein the constricted gasket comprises silicone rubber.

Example 20. The medical system kit of examples 18-19, wherein the constricted gasket is configured to slide along the lead body, wherein the constricted gasket maintains a hemostatic seal between the lead body and the hemostatic valve.

Example 21. The medical system kit of example 20, wherein the inner seal comprises leaflets configured to create the hemostatic seal.

Example 22. The medical system kit of examples 15-21, wherein the implantable medical lead further comprises a balloon proximal of the distal end of the lead body, wherein the hemostasis valve is coupled to the lead body proximal of the balloon.

Example 23. A method of manufacturing a medical system kit comprising: forming implantable medical lead comprising a lead body and a helical electrode at least one of extending or extendable from a distal end of the lead body; forming a hemostasis valve configured to slide along the lead body; coupling the hemostasis valve to the lead body proximal the distal end of the lead body; and placing the implantable medical lead with the hemostasis valve coupled thereto within a package, wherein the distal end of the lead body is configured for insertion into an introducer hub positioned in an opening into a vasculature of a patient and the lead body configured for subsequent advancement through the introducer hub to facilitate securing the hemostasis valve to the introducer hub, wherein the hemostasis valve is configured for slidable advancement of the lead body therethrough for continued advancement of the lead body through the introducer hub.

Example 24. The method of example 23, further comprising placing the introducer hub within the package separated from the hemostasis valve.

Example 25. The method of example 23 or 24, wherein the hemostasis valve extends from a proximal end to a distal end configured for insertion into an opening in the introducer hub, wherein a cross-sectional dimension of the hemostasis valve is tapered from a larger value at the proximal end to a smaller value at the distal end.

Example 26. The method of example 25, wherein the cross-sectional dimension of the proximal end is larger than a corresponding dimension of the opening of the introducer hub.

Example 27. The method of examples 23-26, wherein coupling the hemostasis valve further comprises: constricting a gasket of the hemostasis valve around the lead body, thereby configuring the hemostasis vale to resist blood flow between the gasket and the lead body.

Example 28. The method of example 27, wherein the gasket is configured to slide along the lead body, wherein the gasket is configured to maintain a hemostatic seal between the lead body and the hemostatic valve.

Example 29. The method of examples 23-28, wherein the implantable medical lead further comprises a balloon proximal of the distal end of the lead body, wherein the hemostasis valve is coupled to the lead body proximal of the balloon.

What is claimed is:

1. A medical system comprising:
an implantable medical lead comprising a lead body and a helical electrode at least one of extending or extendable from a distal end of the lead body; and
a hemostasis valve coupled to the lead body proximal the distal end of the lead body, the hemostasis valve coupled to the lead body without insertion of the distal end of the lead body through the hemostasis valve, the hemostasis valve configured to slide along the lead body,
wherein the distal end of the lead body is configured for insertion into an introducer hub positioned in an opening into a vasculature of a patient and the lead body is configured for subsequent advancement through the introducer hub to facilitate securing the hemostasis valve to the introducer hub,
wherein the hemostasis valve is configured to at least one of: slide along an outer surface of the lead body to secure the hemostasis valve to the introducer hub or move distally with the lead body to secure the hemostasis valve to the introducer hub, and
wherein the hemostasis valve is configured for slidable advancement of the lead body therethrough for continued advancement of the lead body through the introducer hub.

2. The medical system of claim 1, wherein the hemostasis valve extends from a proximal end to a distal end configured for insertion into an opening in the introducer hub, wherein a cross-sectional dimension of the hemostasis valve is tapered from a larger value at the proximal end to a smaller value at the distal end.

3. The medical system of claim 2, wherein the cross-sectional dimension of the proximal end of the hemostasis valve is larger than a corresponding dimension of the opening of the introducer hub.

4. The medical system of claim 1, wherein the hemostasis valve further comprises:
a constricted gasket configured to resist blood flow between the gasket and the lead body when coupled to the lead body.

5. The system of claim 1, wherein the hemostasis valve directly contacts the outer surface of the lead body.

6. The medical system of claim 4, wherein the constricted gasket is configured to slide along the lead body, wherein the constricted gasket maintains a hemostatic seal between the lead body and the hemostatic valve.

7. The medical system of claim 6, wherein an inner seal comprises leaflets configured to create the hemostatic seal.

8. The medical system of claim 1, wherein the implantable medical lead further comprises a balloon proximal of the distal end of the lead body, wherein the hemostasis valve is coupled to the lead body proximal of the balloon.

9. A method of using a medical system comprising:
inserting a distal end of a lead into an introducer hub, the lead comprising a lead body, a helical electrode at least one of extending or extendable from the distal end, and a hemostasis valve coupled to the lead body proximal the distal end of the lead;
securing the hemostasis valve to the introducer hub via at least one of sliding the hemostasis valve along the lead body towards the introducer hub or moving the lead body and the hemostasis valve together distally; and
further inserting the lead into the introducer hub positioned in an opening into a vasculature of a patient, wherein the hemostasis valve is configured for slidable advancement of the lead body therethrough for continued advancement of the lead body through the introducer hub.

10. The method of claim 9, wherein securing a hemostasis valve further comprises inserting the hemostasis valve, extending from a proximal end to a distal end, into an opening in the introducer hub, wherein a cross-sectional dimension of the hemostasis valve is tapered from a larger value at the proximal end to a smaller value at the distal end.

11. The method of claim 10, wherein inserting the hemostasis valve is stopped by the cross-sectional dimension of the proximal end being larger than a corresponding dimension of the opening of the introducer hub.

12. The method of claim 9, wherein securing the hemostasis valve further comprises:
constricting a gasket of the hemostasis valve around the lead body, thereby configuring the hemostasis vale to resist blood flow between the gasket and the lead body.

13. The method of claim 9, wherein further inserting the lead further comprises:
sliding an inner seal along the lead body, wherein the inner seal is configured to create a hemostatic seal between the lead body and the hemostatic valve.

14. The method of claim 9, wherein sliding an inner seal does not disrupt the hemostatic seal between the gasket and the lead body.

15. A medical system kit comprising:
an implantable medical lead comprising a lead body and a helical electrode at least one of extending or extendable from a distal end of the lead body;
a hemostasis valve coupled to the lead body proximal the distal end of the lead body, hemostasis valve configured to slide along the lead body; and
a package containing the implantable medical lead with the hemostasis valve coupled thereto,
wherein the distal end of the lead body is configured for insertion into an introducer hub positioned in an opening into a vasculature of a patient and the lead body configured for subsequent advancement through the introducer hub to facilitate securing the hemostasis valve to the introducer hub,
wherein the hemostasis valve is configured for slidable advancement of the lead body therethrough for continued advancement of the lead body through the introducer hub.

16. The medical system kit of claim 15, wherein the hemostasis valve extends from a proximal end to a distal end configured for insertion into an opening in the introducer hub, wherein a cross-sectional dimension of the hemostasis valve is tapered from a larger value at the proximal end to a smaller value at the distal end.

17. The medical system kit of claim 15, wherein the cross-sectional dimension of the proximal end is larger than a corresponding dimension of the opening of the introducer hub.

18. The medical system of claim 15, wherein the hemostasis valve further comprises:

a constricted gasket configured to resist blood flow between the gasket and the lead body when coupled to the lead body.

19. The medical system kit of claim 18, wherein the constricted gasket comprises silicone rubber.

20. The medical system kit of claim 18, wherein the constricted gasket is configured to slide along the lead body, wherein the constricted gasket maintains a hemostatic seal between the lead body and the hemostatic valve.

21. The medical system kit of claim 20, wherein an inner seal comprises leaflets configured to create the hemostatic seal.

22. The medical system kit of claim 15, wherein the implantable medical lead further comprises a balloon proximal of the distal end of the lead body, wherein the hemostasis valve is coupled to the lead body proximal of the balloon.

23. A method of manufacturing a medical system kit comprising:

forming implantable medical lead comprising a lead body and a helical electrode at least one of extending or extendable from a distal end of the lead body;

forming a hemostasis valve configured to slide along the lead body;

coupling the hemostasis valve to the lead body proximal the distal end of the lead body; and placing the implantable medical lead with the hemostasis valve coupled thereto within a package, wherein the distal end of the lead body is configured for insertion into an introducer hub positioned in an opening into a vasculature of a patient and the lead body configured for subsequent advancement through the introducer hub to facilitate securing the hemostasis valve to the introducer hub, wherein the hemostasis valve is configured for slidable advancement of the lead body therethrough for continued advancement of the lead body through the introducer hub.

24. The method of claim 23, further comprising placing the introducer hub within the package separated from the hemostasis valve.

25. The method of claim 23, wherein the hemostasis valve extends from a proximal end to a distal end configured for insertion into an opening in the introducer hub, wherein a cross-sectional dimension of the hemostasis valve is tapered from a larger value at the proximal end to a smaller value at the distal end.

26. The method of claim 25, wherein the cross-sectional dimension of the proximal end is larger than a corresponding dimension of the opening of the introducer hub.

27. The method of claim 23, wherein coupling the hemostasis valve further comprises:

constricting a gasket of the hemostasis valve around the lead body, thereby configuring the hemostasis vale to resist blood flow between the gasket and the lead body.

28. The method of claim 27, wherein the gasket is configured to slide along the lead body, wherein the gasket is configured to maintain a hemostatic seal between the lead body and the hemostatic valve.

29. The method of claim 23, wherein the implantable medical lead further comprises a balloon proximal of the distal end of the lead body, wherein the hemostasis valve is coupled to the lead body proximal of the balloon.

* * * * *